United States Patent [19]

Sugaya et al.

[11] Patent Number: 4,964,059
[45] Date of Patent: Oct. 16, 1990

[54] APPARATUS FOR INSPECTING A PIPELINE

[75] Inventors: Nobuyasu Sugaya; Munetaka Kondo; Kikuji Murashita; Motoi Kobayashi, all of Tokyo, Japan

[73] Assignee: NKK Corporation, Tokyo, Japan

[21] Appl. No.: 232,494

[22] Filed: Aug. 15, 1988

[30] Foreign Application Priority Data

Aug. 21, 1987 [JP] Japan .................................. 62-207981

[51] Int. Cl.$^5$ .......................................... G01N 29/10
[52] U.S. Cl. .................................... 364/507; 73/598; 73/623; 364/563
[58] Field of Search .................. 73/598, 622, 623, 628; 324/229, 237, 240, 242; 364/507, 561, 563; 367/13

[56] References Cited

U.S. PATENT DOCUMENTS

| | | | |
|---|---|---|---|
| 3,205,435 | 9/1965 | Nuttall | 324/229 X |
| 3,810,384 | 5/1974 | Evans | 73/623 X |
| 4,162,635 | 7/1979 | Triplett et al. | 73/623 |
| 4,218,923 | 8/1980 | Triplett et al. | 73/623 |
| 4,285,242 | 8/1981 | Braithwaite | 73/623 |
| 4,353,257 | 10/1982 | Vrba et al. | 73/598 X |
| 4,507,608 | 3/1985 | Flach et al. | 324/237 X |
| 4,675,604 | 6/1987 | Moyer et al. | 324/240 X |

*Primary Examiner*—Parshotam S. Lall
*Assistant Examiner*—Edward R. Cosimano
*Attorney, Agent, or Firm*—Frishauf, Holtz, Goodman & Woodward

[57] ABSTRACT

An apparatus for inspecting a pipeline having a pig body which measures an inner shape and a wall thickness of a pipe body, travelling inside the pipe body, comprises: at least one distance measuring device for measuring a travelling distance of the pig body; a rotation angle gauge for measuring a rotation angle of the pig body round its center axis; a plurality of transducers for transmitting and receiving ultrasonic beams being arranged in the circumferential direction of the pig body and being confronted with the inner surface of the pipe body, which measures the inner shape and the wall thickness of the pipe body; a recorder of the pig body which stores measured data; a signal processing device for processing signals from the distance measuring device, the rotation angle gauge and the transducers; and a data processing device for analyzing the measured data stored in the recorder after the pig body has been taken out of the pipe body.

11 Claims, 7 Drawing Sheets

APPARATUS FOR INSPECTING A PIPELINE

BACKGROUND OF THE INVENTION

1. Field of the Invention

The present invention relates to an apparatus for inspecting a pipeline which measures an inner shape or a wall thickness of a pipeline to inspect a deformation or a corrosion of a pipeline, and more particularly to an apparatus for inspecting a pipeline with ultrasonic beams which inspects a pipeline by detecting an ultrasonic beam signal reflected from a pipe body.

2. Description of the Prior Art

This kind of prior art apparatus is constructed in such a manner that scraper cups are arranged in the front and in the rear of a pig body travelling inside a pipeline and that a pressure difference is made by these scraper cups to propel the pig body by pressure, This apparatus is provided with a travelling distance measuring device which measures a travelling distance of the pig body by counting the number of a rotation of a rotating body being in contact with the inner surface of the pipe body. The apparatus is also provided with a dent-deformation measuring device which measures a deformation of the pipe body by measuring an angle of arms relative to the axis of the pipe body. A plurality of the arms are fitted to the center of the rear of the pig body, extending radially in contact with the inner surface of scraper cups in the rear and moving toward the inside of the pig body when the scraper cups in the rear are transformed in connection with the deformation of the pipe body which is encountered by the scraper cups during a travel of the pig body.

In case of measuring a wall thickness of a pipe body to determine a corrosion state of the pipe body, there are arranged a magnet having North pole and South pole in the axial direction of the pipe body and a magnetic sensor for measuring a change of the densities of the magnetic flux, which is caused by the magnet and changed by the wall thickness of the pipe body, in the vicinity of the inner surface of the pipe body.

In case of measuring an inner shape or a wall thickness of a pipe body, the data collected by the above-mentioned travelling distance measuring device and the dent-deformation measuring device or by a magnetic sensor are recorded in a data recorder inside the pig body. After the pig body is propelled to travel a predetermined distance inside the pipe body to measure a shape of the pipe body and the pig body is taken out of the pipe body, an inner shape of the pipe body is formed by reading out and processing the collected data with the use of a computer.

The prior art apparatus for inspecting a pipeline as mentioned above can determine where a deformation of a pipe body or a change of a wall thickness is in the axial direction of the pipe body by combining the output of the distance measuring device with the output of the dent-deformation measuring device or the magnetic sensor. It is impossible, however, to know where they are in the circumferential direction of the pipe body. As a result, the prior art apparatus has disadvantages in that it is impossible to recognize the shape of the pipe body.

SUMMARY OF THE INVENTION

It is an object of the present invention to provide an apparatus for inspecting a pipeline which can detect a deformation and a distribution of a wall thickness of a pipe body by making clear their positions both in the axial direction and in the circumferential direction.

To accomplish the above-mentioned object, an apparatus for inspecting a pipeline having a pig body which measures an inner shape and a wall thickness of a pipe body, travelling inside the pipe body, includes:

- at least one distance measuring device for measuring a travelling distance of the pig body;
- a rotation angle gauge for measuring a rotation angle of the pig body round its center axis;
- a plurality of transducers for transmitting and receiving ultrasonic beams arranged in the circumferential direction of the pig body and confronted with the inner surface of the pig body, which measures the inner shape and the wall thickness of the pipe body;
- a recorder of the pig body which stores a measured data;
- a signal processing device for processing signals from the distance measuring device, the rotation angle gauge and the transducers for transmitting and receiving ultrasonic beams; and
- a data processing device for analyzing the measured data stored in said recorder after the pig body has been taken out of the pipe body.

DESCRIPTION OF THE PREFERRED EMBODIMENT

Figure 1:
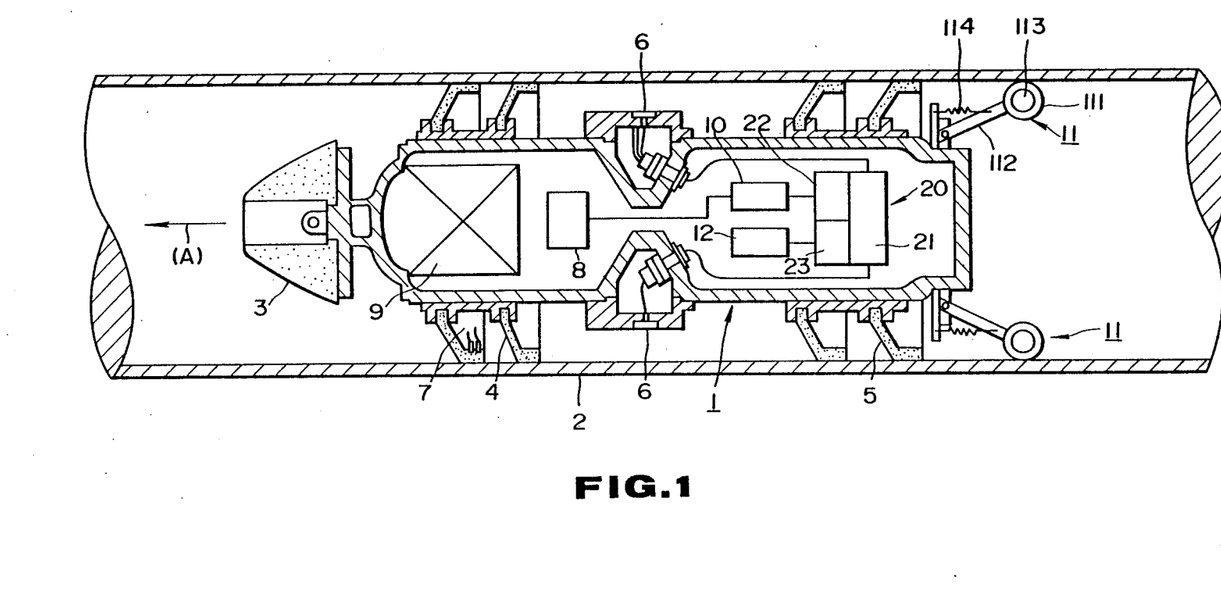
FIG. 1 is a longitudinal sectional view showing schematically a pig body of the present invention.

A preferred embodiment of the present invention will now be explained with specific reference to the attached drawing. FIG. 1 is a longitudinal sectional view illustrating a pig body travelling inside pipe body 2. In the drawing, referential numeral 1 denotes a pig body provided with measuring devices for measuring a shape and a wall thickness of pipe body 2. Pig body 1 is propelled by pressure in the direction shown with an arrow symbol (A). Referential numeral 3 denotes a shock absorber fitted to a head of pig body 1. The shock absorber positioned in the front of pig body 1 has a function of decreasing shock to on-board devices and protecting the devices from damage even if the head of pig body 1 touches a sharp curve or a valve of pipe body 2. At the same time, the valve is also protected.

Referential numerals 4 and 5 denote scraper cups which are set on the outer side in the front and in the rear of pig body 1, extending outwardly, in contact with the inner surface of pipe body 2. Soft and durable synthetic rubber is used for the scraper cups. Even if there is an offset, a deformation or a valve inside the pipe body, the scraper cups have a function of getting over them easily. In addition, being given a difference in pressures between an upper stream side and a lower stream side of pig body 1, the scraper cups have a function of travelling easily inside the pipe body, being propelled directly by the difference in pressures.

Figure 2:
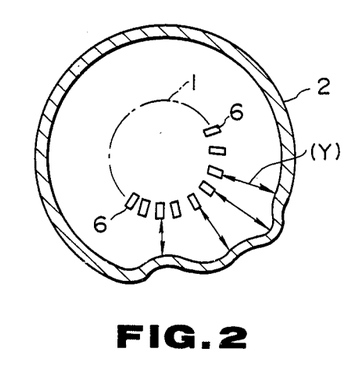
FIG. 2 is a transverse sectional view showing an arrangement of transducers for transmitting and receiving ultrasonic beams of the present invention.

Referential numeral 6 denotes transducers for transmitting and receiving ultrasonic beams. As shown in FIG. 2, the transducers are arranged in the circumferential direction of pig body 1. (Y) shown in FIG. 2 designates a distance between the end of transducer 6 and the inner surface of pipe body 2. This distance is referred to as a water distance. In FIG. 1, referential numeral 8 denotes a recorder such as a magnetic tape or a magnetic disc and 9 a battery power source for supplying a power source required for necessary circuits and devices.

Figure 3:
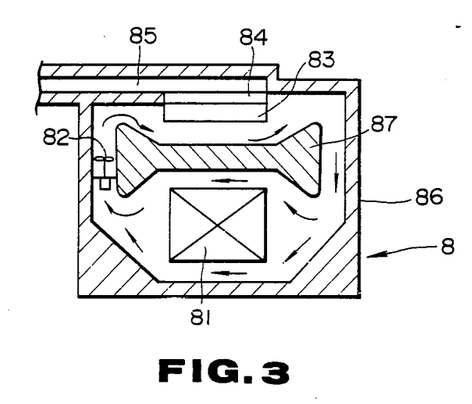
FIG. 3 is a longitudinal sectional view illustrating means for cooling a recorder of the present invention.

A temperature for the use of the magnetic tape or the magnetic disc is 50° C. or less. Therefore, means for cooling is set in recorder 8. This will be explained with specific reference to FIG. 3. FIG. 3 is a longitudinal sectional view showing schematically a structure of recorder 8 shown in FIG. 1. Storage element 81 storing a measured data is enclosed with heat insulation 86. A cooling gas in a space enclosed with the heat insulation is circulated by fan 82 and stream controlling plate 87 in the direction shown with arrow symbols in FIG. 3. The gas circulating in the space is cooled by fin type heat exchanger 83 located above stream controlling plate 87, thermo-electric cooling unit 84 and heat pipe 85. This enables storage element 81 to be kept at a temperature of the limit of using the storage element or less. The end of heat pipe 85 extends outside the pig body to release heat.

Figure 5:
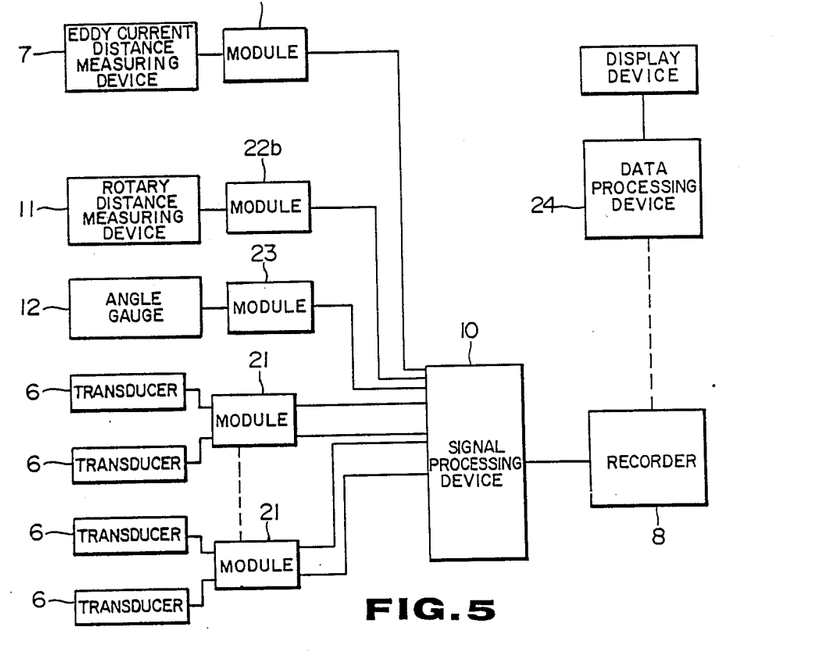
FIG. 5 is a block diagram showing an electrical constitution of an apparatus of the present invention.

In FIG. 1, referential numeral 10 denotes a signal processing device which has a function of taking a signal relating to measured data in, and of selecting it to send to recorder 8. Reference number 20 designates means for amplifying and A/D conversion, including modules 21, 22 and 23. Module 22 further includes modules 22a and 22b as shown in FIG. 5. Module 21 amplifies and provides A/D conversion of signals from transducers 6, module 22a from signal current distance measuring device 7, module 22b from signal rotary distance measuring device 11, and module 23 from signal angle gauge 12, There are also arranged two kinds of distance measuring devices which measure a travelling distance of pig body 1. One of the distance measuring devices is rotary measuring device 11 and the other is eddy current distance measuring device 7. Firstly, rotary distance measuring device 11 will be explained. Distance measuring device 11 is set on the wall surface of pig body 1 behind scraper cup 5. Rotary distance measuring device 11 is comprised of arm 112 extending from an outer wall of pig body 1 outwardly and being provided with roller 111 at its end, of rotation angle gauge 113 measuring a rotation angle of roller 111 and of spring 114 having a function of pushing roller 111 to the inner surface of the pipe body. A signal from rotary distance measuring device 11 is sent to the recorder through signal processing device 10. A plurality of the rotary distance measuring devices are set and the error of a distance which is caused by a bending area of the pipe body is corrected with the use of the output of these distance measuring devices.

Figure 4:
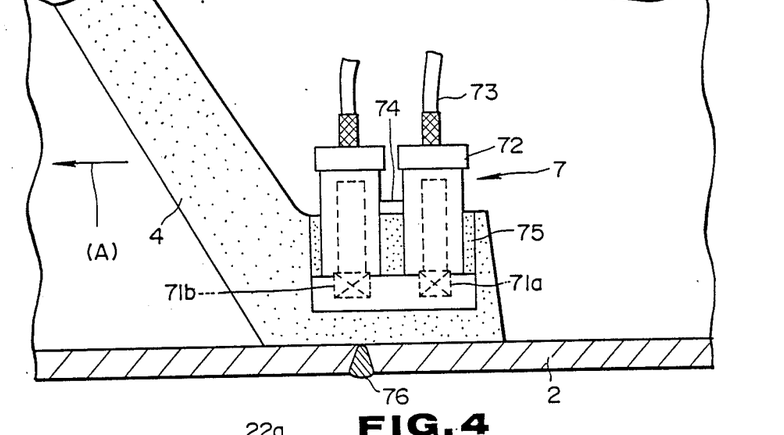
FIG. 4 is a longitudinal sectional view illustrating an enlarged eddy current distance measuring device of the present invention shown in FIG. 1.

Subsequently, eddy current distance measuring device 7 will be explained with specific reference to FIG. 4. Eddy current distance measuring device 7 is set in the vicinity of a position where scraper cup 4 located in the front of the pig body is in contact with pipe body 2. Probe type sensor 72 which has sensor coils 71a and 71b confronted with the inner surface of pipe body 2 is buried in epoxy resin 75. Epoxy resin 75 is fixed to scraper cup 4 by means of keep plate 74. Cable 73 used for supplying a power source and for sending a signal is connected to probe type sensor 72 from the upper side.

The work of the eddy current distance measuring device 7 will now be explained. When impedances of two sensor coils 71a, 71b are $Z_1$ and $Z_2$ respectively, the impedances $Z_1$ and $Z_2$ vary dependent upon the material of pipe body 2 near sensor coils 71a, 71b. Accordingly, when pig body 1 travels in the direction shown with arrow symbol (A) in FIG. 4 and sensor coils 71a, 71b come near weld portion 76, the impedances $Z_1$ and $Z_2$ vary and this enables to detect a position of the weld portion. The reason why two sensor coils 71a, 71b are set is that measuring a difference between impedances $Z_1$ and $Z_2$ enables the sensor coils to be more sensitive to a change of the above-mentioned materials than measuring an individual change of the impedances $Z_1$ or $Z_2$ relative to a distance in the axial direction of the pipe body.

The reason why two kinds of distance measuring devices, namely eddy current distance measuring device 7 and rotary distance measuring device 11, are set will now be explained. Roller 111 in FIG. 1 has a possibility of slipping or running idle dependent upon a deformation or other shapes of the surface inside the pipe body during a travel of the pig body. As a result, errors in the measurement of distances can accumulate. In case an abnormal portion is detected when both of the distance measuring devices work simultaneously, the location of a pipe of the laid pipeline having the abnormal portion can be known in correspondence with the number and numbers of the weld portions by means of eddy current distance measuring device 7 and a correct position of the abnormal portion between the weld portions can be found out by rotary distance device.

In the mentioned embodiment of the distance measuring devices, a plurality of rotary distance measuring devices 11 and eddy current distance measuring device 7 are used. It should, however, be noted that a single rotary distance measuring device 11 can satisfactorily detect a deformation and a distribution of a wall thickness of pipe body 2 without using eddy current distance measuring device 7, although the accurracy is slightly reduced compared with the mentioned embodiment.

In reference to FIG. 1, reference numeral 12 denotes a rotation angle gauge which measures a rotation angle when pig body 1 rotates in the circumferential direction inside the pipe body. Rotation angle gauge 12 comprising a rotation meter and a pendulum measures a rotation angle formed by a base line set in the rotation meter and by the pendulum.

An electrical constitution of the pig body will now be explained with specific reference to FIG. 5. Signals from transducers 6, distance measuring devices 7, 11 and angle gauge 12 are inputted in amplifiers 21, 22a, 22b and 23 and amplified. Thereafter, A/D conversion of these signals are made and the signals come in signal processing device 10.

Signal processing device 10 has a function of generating a keyword signal every time transducers 6 make one round, working successively in the circumferential direction and of supplying to recorder 8 the keyword signal together with the output of distance measuring devices 7 and 11, the output of angle gauge 12 and the number and the output of each transducer. Signal processing device 10 has also a function of selecting signals supplied from amplifiers 21, 22a, 22b and 23 and inputs them in recorder 8. After the measurement finishes, the recorder is taken out of the pig body. A data in the recorder is analyzed with the use of data processing device 24 arranged outside the pipe body to show the data relative to a pipe shape or a wall, thickness of a pipe in a form easy to see on a display 25 with a printer or on a hard copy therefrom.

The number and spacings of transducers 6 fitted to pig body 1 are determined optionally dependent upon a diameter of pipe body 2 which is an object of the measurement, diameter of pig body 1 and the measurement accuracy to be expected. Usually, a plurality of transducers 6 are connected to one of amplifiers 21. Accordingly, the number of amplifiers 21 are determined by an interval between scanning lines and by the number of transducers 6.

To obtain a data of a deformation or a wall thickness of a satisfactory accuracy, the abovementioned interval is preferred to be 20 mm or less. Theoretically, the smaller the interval and the larger the number of the transducers, the higher the measurement accuracy becomes. However, the abovementioned interval is desired to be 5 mm or more, because a space occupied by the transducers is limited; it is desirable to increase relatively the number of amplifiers in order to keep a travelling speed even though there are lots of transducers 6; the number of the amplifiers mounted on pig body 1 is limited relative to the space; and there can occur a problem of cost.

Methods of measuring a water distance which is a distance between the end of transducer 6 and the inner surface of pipe body 2 and of measuring a wall thickness of the pipe body with the use of ultrasonic beams will be explained with specific reference to FIGS. 6 and 7. In the drawings, referential numeral 6 denotes a transducer. Referential numerals 31 and 32 denote an inner surface of a pipe body and an outer surface of the pipe body. T denotes an incident beam, S and B reflecting beams from the inner and outer surfaces of a normal portion, S' and B' reflecting beams from the inner and outer surfaces of an abnormal portion. To explain the work of the ultrasonic beam in terms of time period by using a character symbol, in the following "$t_S$" is used as a period of time during which the incident beams are transmitted toward the normal portion and reflecting beams from the inner surface of the pipe body are received by the transducer. $t_B$ is also used as a period of time during which the incident beams are transmitted toward the normal portion and reflecting beams from the outer surface of the pipe body are received by the transducer. $t'_S$ is used as a period of time during which the incident beams are transmitted toward the abnormal portion and reflecting beams from the inner surface of the pipe body are received. $t'_B$ is used as a period of time during which the incident beams are transmitted toward the abnormal portion and reflecting beams from the outer surface of the pipe body are received by the transducer. These periods of time $t_S$ and $t'_S$ are proportional to the water distance. $(t_B - t_S)$ and $(t'_B - t'_S)$ are proportional respectively to the wall thickness of the normal portion and the abnormal portion.

Figure 6:
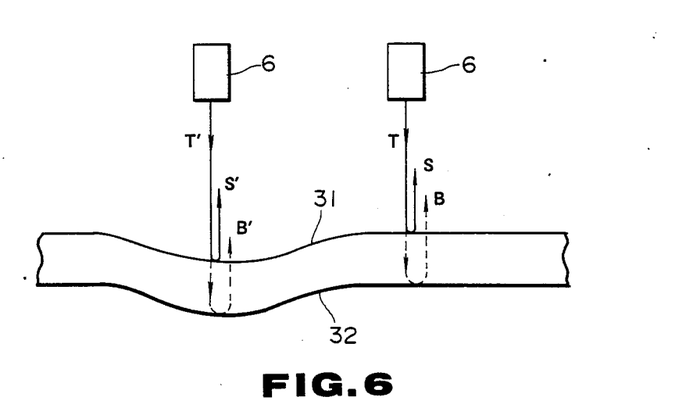
FIGS. 6 and 7 are explanatory views illustrating methods of measuring a water distance and a wall thickness of the pipe body of the present invention respectively.
Figure 7:
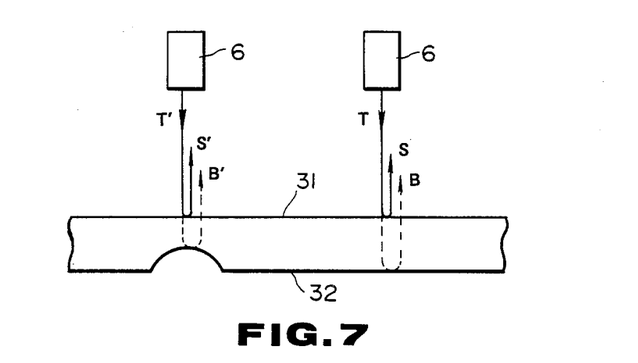

As shown in FIG. 6, in case the wall thickness of the pipe is not changed, but deformed, a degree of a deformation of the inner surface of the pipe can be recognized by comparing $t_S$ with $t'_S$. In this case, it is recognized by comparing $(t_B - t_S)$ with $(t'_B - t'_S)$ whither there is any change of the wall thickness or not. As shown in FIG. 7, in case the inner surface of the pipe body is good and the outer surface of the pipe body has a pitting corrosion, the size of the abovementioned corrosion can be recognized because $(t'_B - t'_S)$ corresponds to the wall thickness of the corrosion portion. In this case, it can be known by comparing $t_S$ with $t'_S$ that the inner surface of the pipe body is good. Signals of the ultrasonic beams transmitted by transducers 6 and reflected from the inner surface and the outer surface of the pipe body together with the signals of the travelling distance and the rotation angle of pig body 1 which are measured by distance measuring device 11 and rotation angle gauge 12 are amplified respectively by amplifiers 21, 22a, 22b and 23. Thereafter, A/D conversion of these signals is made and the converted signals are sent to signal processing device 10.

A method of analyzing shape of a pipe body by means of signals from transducers 6 will be explained with specific reference to FIGS. 8A and 8B. Signals from amplifier 21 are selected on the basis of threshold levels ±St (B) shown in FIG. 8(A). That is to say, a predetermined range of an elevation of a deformation is made to be a normal portion and the deformation which exceeds this range is made to be an abnormal portion.

Figures 8A, 8B:
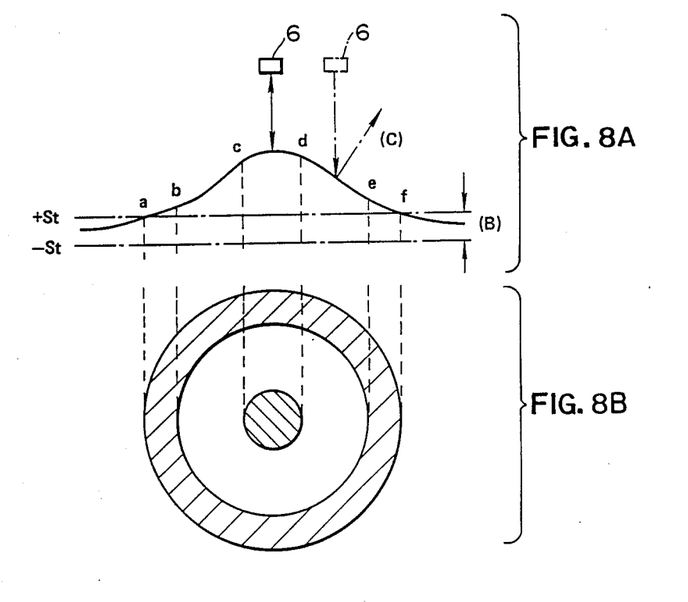
FIGS. 8A and 8B are explanatory views illustrating a method of measuring a shape of the pipe body of the present invention.

As shown in FIG. 8(A), ultrasonic beams transmitted from transducer 6 are reflected in the direction almost opposite to an incident direction of the ultrasonic beams in comparatively flat portions a - b, c - d and e - f on the surface of the pipe body and the reflecting ultrasonic beams can be received by said transducer 6. However, the ultrasonic beams, which reflect in the direction (C) in a comparatively sharply inclined portion b - c and d - e of the inner surface of the pipe body, cannot be received by transducers 6. If the deformation portion of pipe body 2 is drawn in a top plan view, it is understood that the reflecting beams are received in a portion of oblique lines shown in FIG. 8(B).

Signal processing device 10 selects signals of each of transducers 6 on the basis of the abovementioned threshold levels ±St. Every time all the transducers work at least once, signal processing device 10 outputs the selected signals and the number corresponding to the selected signals. Then, the outputted signals and the number are stored in recorder 8.

In this way, the data, being collected successively in the circumferential direction of the pipe body is recorded in recorder 8 by means of a predetermined format. Then, after pig body 1 is taken out of the pipe body, a storage data is read out from recorder 8 by means of data processing device 24 to make a data or a drawing relative to a shape of the pipe body or a shape of a corrosion.

Figure 9:
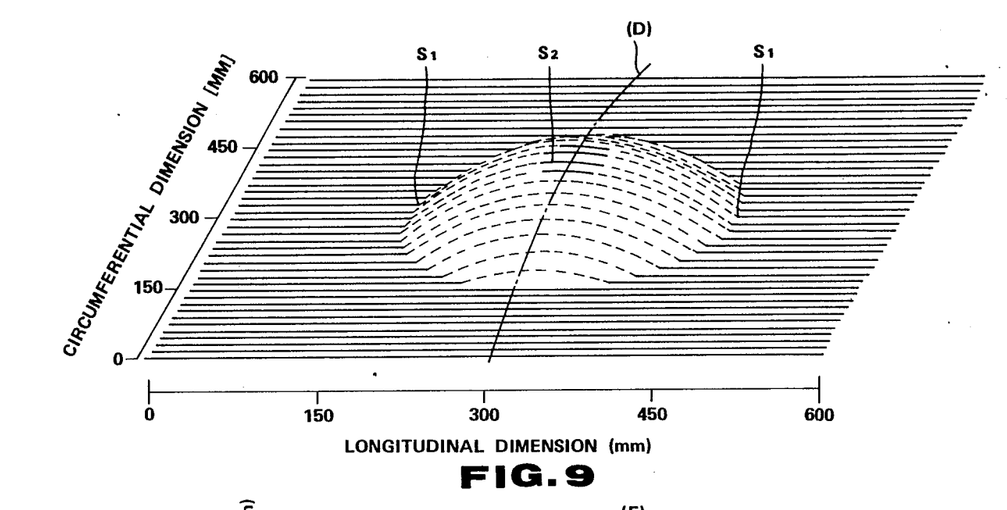
FIG. 9 is an explanatory view illustrating an interpolation by means of which an unknown portion is interpolated, based on a measured data according to the present invention.

FIG. 9 is an explanatory view illustrating an abnormal portion in which a part of the inner surface of the pipe body is convex so as to be seen easily in three dimensions and developing the inner surface of the pipe body on a plane. Lines drawn horizontally and in parallel correspond respectively to scanning lines of each transducer 6. Solid lines designates a known data which can be obtained by a measured data or can be known easily. Dotted lines designate a portion in which transducers 6 cannot receive reflecting beams. An inner shape of the pipe body can be formed by interpolating the portion, in which reflecting beams cannot be received, by means of various kinds of interpolations with the use of the obtained data.

Figure 10:
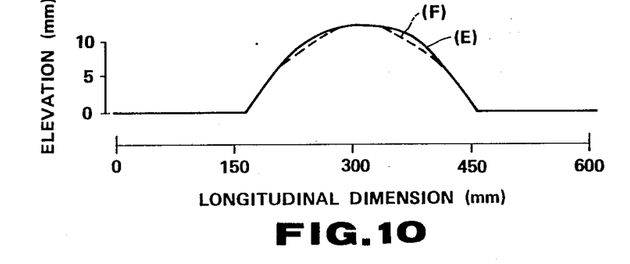
FIG. 10 is a graphic representation comparing an actual shape of the pipe body with a shape obtained with the use of the interpolation according to the present invention.

In FIG. 9, $S_1$, and $S_2$ denote respectively the foot and the top of a convexity in which a data is obtained. Known points of $S_1$ are connected to known points of $S_2$ by prolonging the scanning lines. Relative to portions in which the scanning lines do not pass $S_2$, there is drawn a hypothetical line connecting points at which a plane perpendicular to the scanning lines and passing through the center of $S_2$ crosses the solid lines and, subsequently, there is connected a point of $S_1$ to a point at which a line prolonged from the solid line crosses the hypothetical line (D) shown in FIG. 9. In this way, all the deformation portions can be reproduced. In this connection, a deformation portion was actually made simultaneously inside the pipe body and was measured. As a result, a shape (E) as shown in FIG. 10 was obtained. On the other hand, a shape (F) as shown with dotted lines in FIG. 10 is a deformed shape formed by means of the above-mentioned interpolation with the use of the present apparatus. As it is clearly seen, there is almost not any difference between both shapes. This means that a shape of a pig body having a deformation can be reproduced correctly with the use of the present apparatus.

Distance measuring devices 7 and 11 output an electrical signal in correspondence with a distance of a travel of pig body 1 when pig body 1 is propelled by pressure. Angle gauge 12 outputs an electrical signal in correspondence with a rotation angle when pig body 1 rotates inside the pipe body. These signals are inputted in amplifiers 22a, 22b and 23 and amplified respectively. And A/D conversion of these signals are made. The rotation angle of pig body 1 is not large. A data of a deformation or a wall thickness of the pipe body can be associated with coordinates in the circumferential direction of the pipe body by the data of the rotation angle and the number of the transducers.

Subsequently, an effect caused by the constitution of the embodiment of the present invention will now be explained. The apparatus for inspecting a pipeline with ultrasonic beams is constructed in such a manner that transducers 6 being able to transmit and receive ultrasonic beams are arranged in the circumferential direction of pig body 1 to measure a shape and a wall thickness of a pipe body. Therefore, it is unnecessary to arrange separately transducers for transmitting ultrasonic beams and transducers for receiving ultrasonic beams; coordinates in the circumferential direction can be reproduced correctly in association with the data of angle gauge 12; and it is unnecessary to arrange separately devices for measuring a shape and a wall thickness of the pipe body. This enables the apparatus to decrease cost and to reduce the required space for fitting devices to the apparatus.

Further, the apparatus is constructed in such a manner that threshold levels are set to select a set of data. Therefore, speed-up of collecting the data and a miniaturization of memory capacity can be realized.

Futhermore, the shape of the pipe body having a deformation can be determined with high accuracy.

According to the present invention, pig body 1 having scraper cups is propelled by pressure. However, pig body 1 can be moved with the use of manual, mechanical and other means at a predetermined speed. In this embodiment, the shape of the pipe body is formed with the data processing device outside the pipe body. However, a micro-computer as means for forming an inner shape of a pipe body can be mounted on pig body 1 as occasion arises.

Example

The example of the present invention will now be explained in detail. An outline of pig body 1 is shown in Table 1.

TABLE 1

| | |
|---|---|
| Applicable Pipeline Size | 42", 44", 46" and 48" |
| Overall Length | 3,200 mm (10 feet 6 inches) |
| Total Weight | 3,000 kg (6,600 lbs) |
| Design Pressure | 10 MPa (100 bar) |
| Design Temperature | 70° (158F) |

The pipe of 48 inches in diameter and 20 mm in thickness was scanned by letting pig body 1 travel inside the pipe body to obtain a data of a shape of the pipe body. The results obtained by an analysis of the data are shown in FIGS. 11 and 12.

Figure 11:
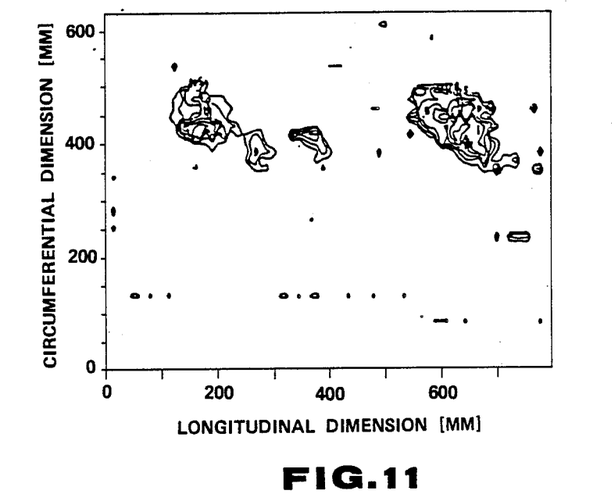
FIG. 11 is a graphic representation showing a measured result with contour lines according to the present invention.
Figure 12:
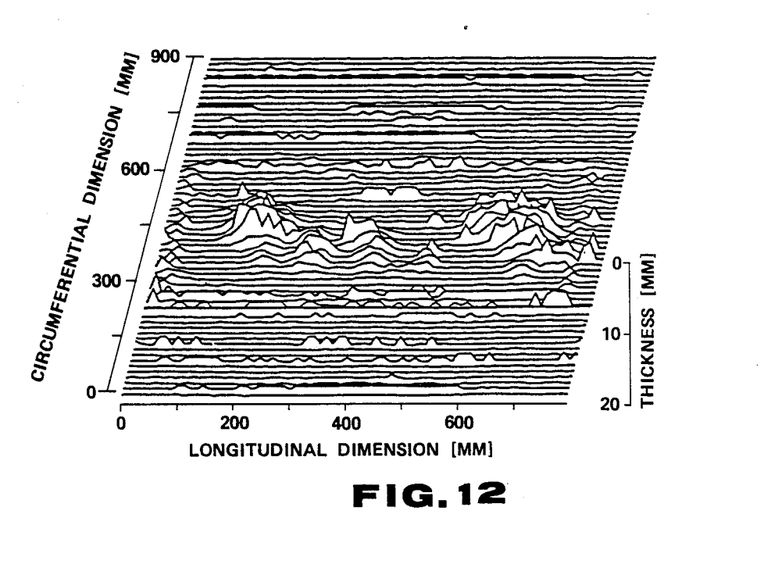
FIG. 12 is a graphic representation showing a measured result of the wall thickness of the pipe body according to the present invention.

FIG. 11 is a graphic representation designated with contour lines which are obtained by measuring the wall thickness of the corroded portion of the pipe body. FIG. 12 is a graphic representation of the measured results illustrated with a three-dimentional map. In FIG. 12, the lines of the patching are observed as rectangular lines of low mountains surrounding high mountains.

The present invention can be carried out in various ways within the range of the essentials of the present invention.

What is claimed is:

1. An apparatus for inspecting a pipeline having a pig body which measures an inner shape and a wall thickness of a pipe body, traveling inside the pipe body, comprising:
   at least one distance measuring device for measuring a traveling distance of the pig body;
   a rotation angle gauge for measuring a rotation angle of the pig body around its center axis;
   a plurality of transducers for transmitting and receiving ultrasonic beams being arranged in the circumferential direction of the pig body and being confronted with the inner surface of the pipe body, for measuring the inner shape and the wall thickness of the pipe body;
   a recorder associated with the pig body which stores measured data;
   a signal processing device for processing signals from the distance measuring device, the rotation angle gauge and the transducers, wherein said signal processing device includes means for interpolating unknown data with obtained signals; and a data processing device for analyzing the measured data stored in said recorder after the pig body has been taken out of the pipe body.

2. The apparatus for inspecting a pipeline of claim 1, wherein said signal processing device includes means for selecting input signals on the basis of predetermined threshold levels.

3. The apparatus for inspecting a pipeline of claim 1, wherein said signal processing device includes means for recording a period of time during which ultrasonic beams are transmitted from the transducers and the ultrasonic beams reflected from the inner surface and the outer surface of the pipe body are received by the transducers.

4. The apparatus for inspecting a pipeline of claim 1, which further comprises means for indicating the inner shape of the pipe body with a graphic representation or a drawing by analyzing the signals recorded an the recorder.

5. The apparatus for inspecting a pipeline of claim 1, wherein the pig body has a unified outer shell.

6. The apparatus for inspecting a pipeline of claim 1, wherein the recorder has means for cooling which comprises thermo-electric elements.

7. The apparatus for inspecting a pipeline of claim 1, wherein the transducers are arranged so that each interval of the scanning lines of the transducers can be from 5 to 20 mm.

8. The apparatus for inspecting a pipeline of claim 1, wherein the at least one distance measuring device includes a rotary distance measuring device.

9. The apparatus for inspecting a pipeline of claim 1, wherein the at least one distance measuring device includes a rotary distance measuring device and an eddy current distance measuring device when the at least one distance measuring device comprises two or more devices.

10. An apparatus for inspecting a pipeline having a pig body which measures an inner shape and a wall thickness of a pipe body, traveling inside the pipe body, comprising:

at least one distance measuring device for measuring a traveling distance of the pig body;

a rotation angle gauge for measuring a rotation angle of the pig body around its center axis;

a plurality of transducers for transmitting and receiving ultrasonic beams being arranged in the circumferential direction of the pig body and being confronted with an inner surface of the pipe body, for measuring the inner shape and the wall thickness of the pipe body;

a recorder associated with the pig body which stores measured data, said recorder having means for cooling which comprises thermo-electric elements;

signal processing device for processing signals from the distance measuring device, the rotation angle gauge and the transducers; and a data processing device for analyzing the measured data stored in said recorder after the pig body has been taken out of the pipe body.

11. An apparatus for inspecting a pipeline having a pig body which measures an inner shape and a wall thickness of a pipe body, traveling inside the pipe body, comprising:

at least two distance measuring devices for measuring a traveling distance of the pig body, including at least a rotary distance measuring device and an eddy current distance measuring device;

a rotation angle gauge for measuring a rotation angle of the pig body around its center axis;

a plurality of transducer for transmitting and receiving ultrasonic beams being arranged in the circumferential direction of the pig body and being confronted with an inner surface of the pipe body, for measuring the inner shape and the wall thickness of the pipe body;

a recorder associated with the pig body which stores measured data;

a signal processing device for processing signals from the distance measuring devices, the rotation angle gauge and the transducers; and a data processing device for analyzing the measured data stored in said recorder after the pig body has been taken out of the pipe body.

* * * * *